United States Patent
Imwinkelried et al.

(10) Patent No.: US 9,469,889 B2
(45) Date of Patent: Oct. 18, 2016

(54) ULTRAPURE MAGNESIUM ALLOY WITH ADJUSTABLE DEGRADATION RATE

(71) Applicant: DePuy Synthes Products, Inc., Raynham, MA (US)

(72) Inventors: Thomas Imwinkelried, Seltisberg (CH); Stefan Beck, Niederdorf (CH); Peter Uggowitzer, Ottenbach (CH); Joerg Loeffler, Greifensee (CH)

(73) Assignee: DePuy Synthes Products, Inc., Raynham, MA (US)

( * ) Notice: Subject to any disclaimer, the term of this patent is extended or adjusted under 35 U.S.C. 154(b) by 518 days.

(21) Appl. No.: 13/827,008

(22) Filed: Mar. 14, 2013

(65) Prior Publication Data

US 2014/0065009 A1 Mar. 6, 2014

Related U.S. Application Data

(60) Provisional application No. 61/695,621, filed on Aug. 31, 2012.

(51) Int. Cl.
| | |
|---|---|
| *C22C 23/04* | (2006.01) |
| *A61L 27/04* | (2006.01) |
| *C22C 23/00* | (2006.01) |
| *C22F 1/06* | (2006.01) |
| *A61L 27/58* | (2006.01) |
| *A61L 31/02* | (2006.01) |
| *A61L 31/14* | (2006.01) |

(52) U.S. Cl.
CPC .............. *C22C 23/04* (2013.01); *A61L 27/047* (2013.01); *A61L 27/58* (2013.01); *A61L 31/022* (2013.01); *A61L 31/148* (2013.01); *C22C 23/00* (2013.01); *C22F 1/06* (2013.01)

(58) Field of Classification Search
CPC .......... C22C 23/00; C22C 23/04; C22F 1/06
See application file for complete search history.

(56) References Cited

U.S. PATENT DOCUMENTS

2012/0095548 A1* 4/2012 Gregorich ............... A61L 27/04
623/1.46

FOREIGN PATENT DOCUMENTS

| CN | 1743486 | 3/2006 | |
|---|---|---|---|
| CN | 1792384 | 6/2006 | |
| CN | 101629260 | 1/2010 | |
| CN | 101658691 | 3/2010 | |
| CN | 101899600 | 12/2010 | |
| EP | 1959025 | 8/2008 | |
| WO | WO 2004013364 | * 2/2004 | ............. C22C 23/02 |
| WO | WO 2012/003522 | 1/2012 | |

OTHER PUBLICATIONS

S. Zhang, X. Zhang, C. Zhao, J. Li, Y. Song, C. Xie, H. Tao, Y. Zhang, Y. He, YJiang, Y. Bian: "Research on an Mg—Zn alloy as a degradable biomaterial", Acta Materialia, No. 6, Jun. 10, 2010, pp. 626-640.
Birbilis et al. "A Combined Neural Network and Mechanistic Approach for the Prediction of Corrosion Rate and Yield Strength of Magnesium-Rare Earth Alloys", Corrosion Science, 53 pp. 168-176, 2011.
Birbilis et al. "On the Corrosion on Binary Magnesium-Rare Earth Alloys", Corrosion Science, 51, pp. 683-689, 2009.
Chia et al. "The Effect of Alloy Composition on the Microstructure and Tensile Properties of Binary Mg-rare Earth Alloys" Intermetallics, 17, pp. 481-490, 2009.
Sudholz et al., "Corrosion Behaviour of Mg-alloy AZ91E With Atypical Alloying Additions", Journal of Alloys and Compounds, 471, pp. 109-115, 2009.
Mendis et al., "An Enhanced Age Hardening Response in Mg_Sn Based Alloys Containing Zn", Materials Science & Engineering, 435-436, pp. 163-171, 2006.
Hanzi et al., Design Consideration for Achieving Simultaneously High-Strength and Highly Ductile Magnesium Alloys, Philosophical Magazine Letters, pp. 1-11, 2012.
Hofstetter et al., "High-Strength Low-Alloy (HSLA) Mg—Zn—Ca Alloys with Excellent Biodegradation Performance" The Minerals, Metals & Materials Society, JOM, vol. 66, No. 4, pp. 566-572, Feb. 2014.
Shaw, "Corrosion Resistance of Magnesium Alloys", ASM Handbook, vol. 13A Corrosion: Fundamentals, Testing, and Protection, pp. 692-696, 2003.
Song, Control of Biodegradation of Biocompatable Magnesium Alloys, Corrosion Science 49, pp. 1696-1701, Feb. 2007.
Yu Sun et al., Preparation and characterization of a new biomedical Mg—Zn—Ca alloy, Materials and Design, vol. 34, pp. 58-64, Feb. 2012.

* cited by examiner

*Primary Examiner* — Jessee Roe
(74) *Attorney, Agent, or Firm* — Baker & Hostetler LLP

(57) ABSTRACT

An alloy and an implant having a three-dimensional structure based on such alloy. The alloy comprises a monophasic MgZn alloy containing from 2.0 wt. % Zn to 6 wt. % Zn, having less than 0.001 wt. % of one or more other elements with the remainder being Mg. In some embodiments, the alloy is substantially free of microgalvanic elements. In some embodiments, the alloy includes a MgZnCa alloy containing nanosized precipitates being less noble than the Mg matrix alloy and having a Zn content ranging from 3.0 wt. % Zn to 6 wt. % Zn and a calcium content ranging from 0.0005 wt. % to 1.0 wt. %, having less than 0.001 wt. % of one or more other elements with the remainder being Mg. In other embodiments, the alloy includes a MgZnCa alloy containing nanosized precipitates being less noble than the Mg matrix alloy, a plurality of nanosized precipitates being more noble than the Mg matrix and having a Zn content ranging from 3.0 wt. % Zn to 6 wt. % Zn, a calcium content ranging from 0.0005 wt. % to 1.0 wt. %, having less than 0.001 wt. % of one or more other elements with the remainder being Mg.

15 Claims, No Drawings

ULTRAPURE MAGNESIUM ALLOY WITH ADJUSTABLE DEGRADATION RATE

This application claims benefit of priority from U.S. Provisional Patent Application No. 61/695,621, filed 31 Aug. 2012, all of which are incorporated by reference herein by in its entirety.

FIELD OF THE INVENTION

The present invention is directed to magnesium alloys having improved degradation properties.

BACKGROUND OF THE INVENTION

Magnesium implants were clinically used for the treatment of bone fractures by several surgeons back in the 1930s. For instance, J. Verbrugge (1934) used both, pure magnesium and Mg-8% Al alloy implants on 21 patients. However, after the Second World War, the use of magnesium as a resorbable implant material declined. In recent years, researchers have renewed their interest in resorbable magnesium implants. A main focus of magnesium research is the development of alloys and coatings. The major goals are to control the degradation rate, to avoid the formation of gas bubbles during degradation and to avoid potentially harmful alloying elements. Therefore, a need exists for magnesium alloys whose rate of degradation can be controlled and/or tuned as desired.

Commercial grade pure magnesium (3N—Mg) does not exhibit uniform degradation in vitro or in vivo. It is believed that the presence of impurities in the commercial product increases the degradation rate due to the formation of microgalvanic elements, including iron (Fe), copper (Cu) and nickel (Ni). Accordingly, a need exists for ultrapure magnesium material for medical applications, including surgical implants.

In order to forestall secondary phases, other contaminants such as cobalt (Co), silicon (Si), manganese (Mn) and aluminum (Al) also need to be controlled. Often times, the presence of a single contaminant can decrease the solubility limit of the other contaminants. The presence of these trace elements can shift the eutectic temperature within the magnesium phase diagram. During the solidification process, the contaminants can accumulate in the interdendritic spaces and induce the formation of secondary phases. These phases cannot be eliminated by subsequent thermomechanical treatments.

Embodiments of the present invention overcome one or more of above-noted challenges.

BRIEF SUMMARY OF THE INVENTION

The present disclosure provides several exemplary embodiments of the present invention, some of which are discussed below.

In an aspect, the present invention provides an alloy composition and an implant having a three-dimensional structure based on such alloy composition. In one embodiment, the composition includes a monophasic MgZn alloy containing from 2.0 wt. % Zn to 6 wt. % Zn, less than 0.001 wt. % of one or more other elements located in a secondary phase and with the remainder being Mg. In one embodiment, the alloy is substantially free of microgalvanic elements. In another exemplary embodiment, the composition consists essentially of a monophasic MgZn alloy containing from 2.0 wt. % Zn to 6 wt. % Zn, less than 0.001 wt. % of one or more other elements located in a secondary phase and with the remainder being Mg. In one such embodiment, the alloy is substantially free of microgalvanic elements. In yet another exemplary embodiment, the composition consist of a monophasic MgZn alloy containing from 2.0 wt. % Zn to 6 wt. % Zn, less than 0.001 wt. % of one or more other elements located in a secondary phase and with the remainder being Mg. In one such embodiment, the alloy is substantially free of microgalvanic elements.

In one embodiment, the MgZn alloy contains less than 5 ppm of total other elements. In another embodiment, the MgZn alloy contains less than 2 ppm of total other elements. In yet another embodiment, the MgZn alloy contains less than 1 ppm of total other elements. In still yet another embodiment, the MgZn alloy contains less than 0.5 ppm of total other elements.

In another embodiment, the composition includes a MgZnCa alloy containing nanosized precipitates being less noble than a MgZn alloy and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase, and with the remainder being Mg. In another embodiment, the composition consists essentially of a MgZnCa alloy containing noble nanosized precipitates being less noble than a MgZn alloy and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg. In another embodiment, the composition consists of a MgZnCa alloy containing nanosized precipitates being less noble than a MgZn alloy and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg.

In one embodiment, the MgZnCa alloy contains less than 5 ppm of total other elements. In another embodiment, the MgZnCa alloy contains less than 2 ppm of total other elements. In yet another embodiment, the MgZnCa alloy contains less than 1 ppm of total other elements. In still yet another embodiment, the MgZnCa alloy contains less than 0.5 ppm of total other elements.

In some other such embodiments, the less noble nanosized precipitates comprise $Mg_6Zn_3Ca_2$.

In another embodiment, the composition includes a MgZnCa alloy containing nanosized precipitates and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase, and with the remainder being Mg and wherein the nanosized precipitates being less noble than the Mg remainder. In another embodiment, the composition consists essentially of a MgZnCa alloy containing noble nanosized precipitates and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg and wherein the nanosized precipitates being less noble than the Mg remainder. In another embodiment, the composition consists of a MgZnCa alloy containing nanosized precipitates and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg and wherein the nanosized precipitates being less noble than the Mg remainder.

In one embodiment, the MgZnCa alloy contains less than 5 ppm of total other elements. In another embodiment, the MgZnCa alloy contains less than 2 ppm of total other elements. In yet another embodiment, the MgZnCa alloy contains less than 1 ppm of total other elements. In still yet another embodiment, the MgZnCa alloy contains less than 0.5 ppm of total other elements.

In some other such embodiments, the less noble nanosized precipitates comprise $Mg_6Zn_3Ca_2$.

In another embodiment, the composition includes a MgZnCa alloy containing nanosized precipitates being less noble than a MgZn alloy, a plurality of nanosized precipitates being more noble than a MgZn alloy, and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase with the remainder being Mg. In another embodiment, the composition consists essentially of a MgZnCa alloy containing nanosized precipitates being less noble than a MgZn alloy, a plurality of nanosized precipitates being more noble than a MgZn alloy, and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg. In another embodiment, the composition consists of a MgZnCa alloy containing nanosized precipitates being less noble than a MgZn alloy, a plurality of nanosized precipitates being more noble than the Mg matrix, and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg.

In one embodiment, the MgZnCa alloy contains less than 5 ppm of total other elements. In another embodiment, the MgZnCa alloy contains less than 2 ppm of total other elements. In yet another embodiment, the MgZnCa alloy contains less than 1 ppm of total other elements. In still yet another embodiment, the MgZnCa alloy contains less than 0.5 ppm of total other elements.

In some such embodiments, the less noble than Mg nanosized precipitates comprise $Mg_6Zn_3Ca_2$. In other such embodiments, the nanosized precipitates being more noble than the Mg matrix comprise Mn—Zn.

In some embodiments of the alloys according to the present invention, each alloy has a grain size of less than 10 μm. In some alloys of present invention, each alloy has a yield strength of at least 200 MPa. In some embodiments, each alloy has a yield strength of at least 200 MPa. In one embodiment, each alloy has an ultimate tensile strength of at least 250 MPa. In another embodiment, each alloy has at least 15% elongation at break. In yet another embodiment, each alloy has an in vitro degradation rate of less than 0.5 mg/cm$^2$ day as measured in a simulated body fluid.

In other embodiments, the implant is an orthopedic implant. In such embodiments, the orthopedic implant comprises one or more of the following: a nail, a screw, a staple, a plate, a rod, a tack, a bolt, a bolt to lock and IM nail, an anchor, a dowel, a plug, a peg, a sleeve, a mesh, a transconnector, a nut, a shaped body, spinal cage, a wire, a K-wire, a woven structure, clamp, splint, scaffold, foam and honeycomb structure. In some other embodiments, the implant has a lower degradation rate compared to magnesium alloy implants containing microgalvanic impurities.

In other embodiments, the implant is a non-orthopedic implant. In such embodiments, the non-orthopedic includes a cardiovascular stent, a neuro stent and a vertebroplasty stent.

In yet another embodiment of the implant, each alloy has an in vitro degradation rate of less than 0.5 mg/cm$^2$ day as measured in a simulated body fluid.

In an aspect, the present invention provides a method of producing an alloy according to the embodiments described herein. In one embodiment, the method comprises: (a) casting a alloy containing (i) ultrapure magnesium having a purity of at least 99.997 wt. % and having less than 0.001 wt. % of one or more other elements; and (ii) from 2.0 to 6 wt. % zinc having a purity of at least 99.999 wt. %, said casting being performed in an inert atmosphere and an inert reaction vessel; (b) heating the cast alloy at two different temperatures wherein a first temperature is below an eutectic temperature of Mg—Zn and a second temperature is above the eutectic temperature of the ternary Mg—Zn—Ca system to thereby form a monophasic MgZn alloy containing from 2.0 wt. % Zn to 6 wt. % Zn, having less than 0.001 wt. % of one or more other elements with the remainder being Mg; and (c) extruding the alloy into a desired shape.

In some embodiments, the method of producing an alloy according to the present invention comprises: (a) casting a alloy containing (i) ultrapure magnesium having a purity of at least 99.997 wt. % and having less than 0.001 wt. % of one or more other elements; (ii) from 3.0 wt. zinc to 6 wt. % zinc having a purity of at least 99.999 wt. %; and (iii) from 0.02 wt. % to 1.0 wt. % calcium metal having a purity of at least 99.9 wt. %, said casting being performed in an inert atmosphere and an inert reaction vessel; (b) heating the cast alloy at two different temperatures wherein a first temperature is below an eutectic temperature of Mg—Zn and a second temperature is above the eutectic temperature of the ternary Mg—Zn—Ca system to thereby form a MgZnCa alloy containing from 3.0 wt. % Zn to 6 wt. % Zn; and a calcium content ranging from 0.0005 wt. % to 1.0 wt. %, with having less than 0.001 wt. % of one or more other elements and the remainder being Mg; (c) extruding the alloy into a desired shape; and (d) heating the shaped alloy to at least 140° C. to form more noble nanosized precipitates dispersed throughout a MgZnCa alloy. In a further embodiment, the method comprises heating to at least 230° C. to form more noble precipitates dispersed throughout a MgZn alloy.

DETAILED DESCRIPTION OF THE INVENTION

Reference will now be made in detail to the various embodiments of the present disclosure.

In an aspect, the present invention relates to a composition comprising a high purity magnesium alloy. In one embodiment, an alloy composition comprises a monophasic MgZn alloy containing from 2.0 wt. % Zn to 6 wt. % Zn, having less than 0.001 wt. % of one or more other elements and with the remainder being Mg. In another embodiment, the alloy composition consists essentially of a monophasic MgZn alloy containing from 2.0 wt. % Zn to 6 wt. % Zn, having less than 0.001 wt. % of one or more other elements and with the remainder being Mg. In yet another embodiment, the alloy composition consists of a monophasic MgZn alloy containing from 2.0 wt. % Zn to 6 wt. % Zn, having less than 0.001 wt. % of one or more other elements and with the remainder being Mg. In some such embodiments, the monophasic MgZn alloy is substantially free of microgalvanic elements.

In another aspect, the present invention relates to an implant composition made from a high purity magnesium alloy. In one embodiment, the implant having a three-dimensional structure comprises a monophasic MgZn alloy containing from 2.0 wt. % Zn to 6 wt. % Zn, having less than 0.001 wt. % of one or more other elements and with the remainder being Mg. In another embodiment, the implant has a three-dimensional structure and comprises a composition consisting essentially of a monophasic MgZn alloy containing from 2.0 wt. % Zn to 6 wt. % Zn, having less than 0.001 wt. % of one or more other elements and with the remainder being Mg. In yet another embodiment, the implant has a three-dimensional structure and comprises a composition consisting of a monophasic MgZn alloy containing from 2.0 wt. % Zn to 6 wt. % Zn, having less than 0.001 wt. % of one or more other elements with the remainder being Mg. In some such embodiments, the monophasic MgZn alloy is substantially free of microgalvanic elements.

Generally, the Zn content in the Mg—Zn alloy and a Mg—Zn alloy used in an implant composition, according to the present invention can range from 2 wt. % to 6 wt. %. In an embodiment, the alloy has Zn content which may be independent selected from ranges from 2 wt. % to 3 wt. %, from 2.1 wt. % to 3 wt. %, from 2.2 wt. % to 3 wt. %, from 2.3 wt. % to 3 wt. %, from 2.4 wt. % to 3 wt. %, from 2.5 wt. % to 3 wt. %, from 2.6 wt. % to 3 wt. %, from 2.7 wt. % to 3 wt. %, from 2.8 wt. % to 3 wt. %, from 2.9 wt. % to 3 wt. %, from 2 wt. % to 4 wt. %, from 2.1 wt. % to 4 wt. %, from 2.2 wt. % to 4 wt. %, from 2.3 wt. % to 4 wt. %, from 2.4 wt. % to 4 wt. %, from 2.5 wt. % to 4 wt. %, from 2.6 wt. % to 4 wt. %, from 2.7 wt. % to 4 wt. %, from 2.8 wt. % to 4 wt. %, from 2.9 wt. % to 4 wt. %, from 3 wt. % to 4 wt. %, from 3.1 wt. % to 4 wt. %, from 3.2 wt. % to 4 wt. %, from 3.3 wt. % to 4 wt. %, from 3.4 wt. % to 4 wt. %, from 3.5 wt. % to 4 wt. %, from 3.6 wt. % to 4 wt. %, from 3.7 wt. % to 4 wt. %, from 3.8 wt. % to 4 wt. %, from 3.9 wt. % to 4 wt. %, from 2 wt. % to 5 wt. %, from 2.1 wt. % to 5 wt. %, from 2.2 wt. % to 5 wt. %, from 2.3 wt. % to 5 wt. %, from 2.4 wt. % to 5 wt. %, from 2.5 wt. % to 5 wt. %, from 2.6 wt. % to 5 wt. %, from 2.7 wt. % to 5 wt. %, from 2.8 wt. % to 5 wt. %, from 2.9 wt. % to 5 wt. %, from 3 wt. % to 5 wt. %, from 3.1 wt. % to 5 wt. %, from 3.2 wt. % to 5 wt. %, from 3.3 wt. % to 5 wt. %, from 3.4 wt. % to 5 wt. %, from 3.5 wt. % to 5 wt. %, from 3.6 wt. % to 5 wt. %, from 3.7 wt. % to 5 wt. %, from 3.8 wt. % to 5 wt. %, from 3.9 wt. % to 5 wt. %, from 4 wt. % to 5 wt. %, from 4.1 wt. % to 5 wt. %, from 4.2 wt. % to 5 wt. %, from 4.3 wt. % to 5 wt. %, from 4.4 wt. % to 5 wt. %, from 4.5 wt. % to 5 wt. %, from 4.6 wt. % to 5 wt. %, from 4.7 wt. % to 5 wt. %, from 4.8 wt. % to 5 wt. %, from 4.9 wt. % to 5 wt. %, from 2 wt. % to 6 wt. %, from 2.1 wt. % to 6 wt. %, from 2.2 wt. % to 6 wt. %, from 2.3 wt. % to 6 wt. %, from 2.4 wt. % to 6 wt. %, from 2.5 wt. % to 6 wt. %, from 2.6 wt. % to 6 wt. %, from 2.7 wt. % to 6 wt. %, from 2.8 wt. % to 6 wt. %, from 2.9 wt. % to 6 wt. %, from 3 wt. % to 6 wt. %, from 3.1 wt. % to 6 wt. %, from 3.2 wt. % to 6 wt. %, from 3.3 wt. % to 6 wt. %, from 3.4 wt. % to 6 wt. %, from 3.5 wt. % to 6 wt. %, from 3.6 wt. % to 6 wt. %, from 3.7 wt. % to 6 wt. %, from 3.8 wt. % to 6 wt. %, from 3.9 wt. % to 6 wt. %, from 4 wt. % to 6 wt. %, from 4.1 wt. % to 6 wt. %, from 4.2 wt. % to 6 wt. %, from 4.3 wt. % to 6 wt. %, from 4.4 wt. % to 6 wt. %, from 4.5 wt. % to 6 wt. %, from 4.6 wt. % to 6 wt. %, from 4.7 wt. % to 6 wt. %, from 4.8 wt. % to 6 wt. %, from 4.9 wt. % to 6 wt. %, from 5 wt. % to 6 wt. %, from 5.1 wt. % to 6 wt. %, from 5.2 wt. % to 6 wt. %, from 5.3 wt. % to 6 wt. %, from 5.4 wt. % to 6 wt. %, from 5.5 wt. % to 6 wt. %, from 5.6 wt. % to 6 wt. %, from 5.7 wt. % to 6 wt. %, from 5.8 wt. % to 6 wt. %, or from 5.9 wt. % to 6 wt. %.

In another embodiment of the present invention, an MgZnCa alloy comprises a plurality of nanosized precipitates being less noble than a MgZn alloy, a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In yet another embodiment, the MgZnCa alloy consists essentially of a plurality of nanosized precipitates alloy being less noble than a MgZn alloy, has a Zn content ranging from 3.0 wt. % Zn to 6 wt. % Zn, a calcium content ranging from 0.0005 wt. % to 0.25 wt. %, has less than 0.001 wt. % of one or more other elements, with the remainder being Mg. In another embodiment, a MgZnCa alloy consists of a plurality of nanosized precipitates alloy being less noble than a MgZn alloy, having a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In some such embodiments, the nanosized precipitates, being less noble than less noble than Mg—Zn, comprise $Mg_6Zn_3Ca_2$.

In another embodiment of the implant of the present invention, the implant has a three-dimensional structure and comprises a MgZnCa alloy. In an embodiment, the implant has a three-dimensional structure made from a MgZnCa alloy comprising a plurality of nanosized precipitates being less noble than a MgZn alloy, has a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In another embodiment, the implant has a three-dimensional structure and comprises a composition consisting essentially of a MgZnCa alloy containing a plurality of nanosized precipitates being less noble than a MgZn alloy, has a Zn content ranging from 3.0 wt. % Zn to 6 wt. % Zn, a calcium content ranging from 0.0005 wt. % to 1.0 wt. %, having less than 0.001 wt. % of one or more other elements, with the remainder being Mg. In another embodiment, the implant has a three-dimensional structure and comprises a composition consisting of a MgZnCa alloy containing a plurality of nanosized precipitates being less noble than a MgZn alloy, has a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In such embodiments, the less noble nanosized precipitates comprise $Mg_6Zn_3Ca_2$.

One of skill in the art will understand that a precipitate that is less noble than Mg—Zn will necessarily be less noble than Mg because Mg—Zn is more noble than Mg. Therefore the above such embodiments of MgZnCa and implants made from same can also be expressed as follows. In another embodiment, the composition includes a MgZnCa alloy containing nanosized precipitates and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase, and with the remainder being Mg and wherein the nanosized precipitates being less noble than the Mg remainder. In another embodiment, the composition consists essentially of a MgZnCa alloy containing noble nanosized precipitates and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg and wherein the nanosized precipitates being less noble than the Mg remainder. In another embodiment, the composition consists of a MgZnCa alloy containing nanosized precipitates and having a Zn content ranging from 3.0 wt. % Zn to 6 wt. % Zn and a calcium content ranging from 0.0005 wt. % to 1.0 wt. %, less than 0.001 wt. % of one or more other elements located in a secondary phase and with the remainder being Mg and wherein the nanosized precipitates being less noble than the Mg remainder.

In yet another embodiment, a MgZnCa alloy comprises a plurality of nanosized precipitates being less noble than a MgZn alloy and a plurality of nanosized precipitates being more noble than a MgZn alloy, a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In another embodiment, a MgZnCa alloy consists essentially of a plurality of nanosized precipitates being less noble than a MgZn alloy and a plurality of nanosized precipitates being more noble than a MgZn alloy, having a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In another embodiment, a MgZnCa alloy consists of a plurality of nanosized precipitates being less noble than a MgZn alloy and a plurality of nanosized precipitates being more noble than a MgZn alloy, having a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In such embodiments, the less noble nanosized precipitates comprise $Mg_6Zn_3Ca_2$ and the more noble nansized precipitates comprise Mg—Zn.

In some other embodiments, an implant in accordance with the present invention has a three-dimensional structure and comprises a MgZnCa alloy having plurality of nanosized precipitates being less noble than a MgZn alloy and a plurality of nanosized precipitates being more noble than a MgZn alloy. In one embodiment, the implant has a three dimensional structure and comprising a composition comprising of a MgZnCa alloy containing a plurality of nanosized precipitates being less noble than a MgZn alloy and a plurality of nanosized precipitates being more noble than a MgZn alloy, and has a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In another embodiment, the implant has a three-dimensional structure and comprises a composition consisting essentially of a MgZnCa alloy containing a plurality of nanosized precipitates being less noble than a MgZn alloy and a plurality of nanosized precipitates being more noble than a MgZn alloy, has a Zn content ranging from 3.0 wt. % Zn to 6 wt. % Zn, a calcium content ranging from 0.0005 wt. % to 1.0 wt. %, has less than 0.001 wt. % of one or more other elements, with the remainder being Mg. In another embodiment, the implant has a three-dimensional structure and comprises a composition consisting of a MgZnCa alloy containing a plurality of nanosized precipitates being less noble than a MgZn alloy and a plurality of nanosized precipitates being more noble than a MgZn alloy, has a Zn content ranging from 3.0 wt. % Zn to 6 wt. % Zn, a calcium content ranging from 0.0005 wt. % to 1.0 wt. %, and hasless than 0.001 wt. % of one or more other elements, with the remainder being Mg. In some such embodiments, the less noble than Mg nanosized precipitates comprise $Mg_6Zn_3Ca_2$. In other such embodiments, the nanosized precipitates being more noble than the Mg matrix comprise Mn—Zn.

Generally, the Zn content in the various embodiments of the MgZnCa alloy and an implant based on the various embodiments of the MgZnCa alloy, according to the present invention, can be any suitable amount. In an embodiment, the MgZnCa alloy has Zn content which may be independent selected from ranges from 2 wt. % to 3 wt. %, from 2.1 wt. % to 3 wt. %, from 2.2 wt. % to 3 wt. %, from 2.3 wt. % to 3 wt. %, from 2.4 wt. % to 3 wt. %, from 2.5 wt. % to 3 wt. %, from 2.6 wt. % to 3 wt. %, from 2.7 wt. % to 3 wt. %, from 2.8 wt. % to 3 wt. %, from 2.9 wt. % to 3 wt. %, from 2 wt. % to 4 wt. %, from 2.1 wt. % to 4 wt. %, from 2.2 wt. % to 4 wt. %, from 2.3 wt. % to 4 wt. %, from 2.4 wt. % to 4 wt. %, from 2.5 wt. % to 4 wt. %, from 2.6 wt. % to 4 wt. %, from 2.7 wt. % to 4 wt. %, from 2.8 wt. % to 4 wt. %, from 2.9 wt. % to 4 wt. %, from 3 wt. % to 4 wt. %, from 3.1 wt. % to 4 wt. %, from 3.2 wt. % to 4 wt. %, from 3.3 wt. % to 4 wt. %, from 3.4 wt. % to 4 wt. %, from 3.5 wt. % to 4 wt. %, from 3.6 wt. % to 4 wt. %, from 3.7 wt. % to 4 wt. %, from 3.8 wt. % to 4 wt. %, from 3.9 wt. % to 4 wt. %, from 2 wt. % to 5 wt. %, from 2.1 wt. % to 5 wt. %, from 2.2 wt. % to 5 wt. %, from 2.3 wt. % to 5 wt. %, from 2.4 wt. % to 5 wt. %, from 2.5 wt. % to 5 wt. %, from 2.6 wt. % to 5 wt. %, from 2.7 wt. % to 5 wt. %, from 2.8 wt. % to 5 wt. %, from 2.9 wt. % to 5 wt. %, from 3 wt. % to 5 wt. %, from 3.1 wt. % to 5 wt. %, from 3.2 wt. % to 5 wt. %, from 3.3 wt. % to 5 wt. %, from 3.4 wt. % to 5 wt. %, from 3.5 wt. % to 5 wt. %, from 3.6 wt. % to 5 wt. %, from 3.7 wt. % to 5 wt. %, from 3.8 wt. % to 5 wt. %, from 3.9 wt. % to 5 wt. %, from 4 wt. % to 5 wt. %, from 4.1 wt. % to 5 wt. %, from 4.2 wt. % to 5 wt. %, from 4.3 wt. % to 5 wt. %, from 4.4 wt. % to 5 wt. %, from 4.5 wt. % to 5 wt. %, from 4.6 wt. % to 5 wt. %, from 4.7 wt. % to 5 wt. %, from 4.8 wt. % to 5 wt. %, from 4.9 wt. % to 5 wt. %, from 2 wt. % to 6 wt. %, from 2.1 wt. % to 6 wt. %, from 2.2 wt. % to 6 wt. %, from 2.3 wt. % to 6 wt. %, from 2.4 wt. % to 6 wt. %, from 2.5 wt. % to 6 wt. %, from 2.6 wt. % to 6 wt. %, from 2.7 wt. % to 6 wt. %, from 2.8 wt. % to 6 wt. %, from 2.9 wt. % to 6 wt. %, from 3 wt. % to 6 wt. %, from 3.1 wt. % to 6 wt. %, from 3.2 wt. % to 6 wt. %, from 3.3 wt. % to 6 wt. %, from 3.4 wt. % to 6 wt. %, from 3.5 wt. % to 6 wt. %, from 3.6 wt. % to 6 wt. %, from 3.7 wt. % to 6 wt. %, from 3.8 wt. % to 6 wt. %, from 3.9 wt. % to 6 wt. %, from 4 wt. % to 6 wt. %, from 4.1 wt. % to 6 wt. %, from 4.2 wt. % to 6 wt. %, from 4.3 wt. % to 6 wt. %, from 4.4 wt. % to 6 wt. %, from 4.5 wt. % to 6 wt. %, from 4.6 wt. % to 6 wt. %, from 4.7 wt. % to 6 wt. %, from 4.8 wt. % to 6 wt. %, from 4.9 wt. % to 6 wt. %, from 5 wt. % to 6 wt. %, from 5.1 wt. % to 6 wt. %, from 5.2 wt. % to 6 wt. %, from 5.3 wt. % to 6 wt. %, from 5.4 wt. % to 6 wt. %, from 5.5 wt. % to 6 wt. %, from 5.6 wt. % to 6 wt. %, from 5.7 wt. % to 6 wt. %, from 5.8 wt. % to 6 wt. %, or from 5.9 wt. % to 6 wt. %.

Generally, the Ca content in the various embodiments of the MgZnCa alloy and in an implant based on the various embodiments of the MgZnCa alloy, according to the present invention, can be any suitable amount. In an embodiment, the MgZnCa alloy has Ca content which may be independent selected from ranges from 0.0005 wt. % to 0.0055 wt. %, from 0.0005 wt. % to 0.0105 wt. %, from 0.0005 wt. % to 0.0155 wt. %, from 0.0005 wt. % to 0.0205 wt. %, from 0.0005 wt. % to 0.0255 wt. %, from 0.0005 wt. % to 0.0305 wt. %, from 0.0005 wt. % to 0.0355 wt. %, from 0.0005 wt. % to 0.0405 wt. %, from 0.0005 wt. % to 0.0455 wt. %, from 0.0005 wt. % to 0.0505 wt. %, from 0.0005 wt. % to 0.0555 wt. %, from 0.0005 wt. % to 0.0605 wt. %, from 0.0005 wt. % to 0.0655 wt. %, from 0.0005 wt. % to 0.0705 wt. %, from 0.0005 wt. % to 0.0755 wt. %, from 0.0005 wt. % to 0.0805 wt. %, from 0.0005 wt. % to 0.0855 wt. %, from 0.0005 wt. % to 0.0905 wt. %, from 0.0005 wt. % to 0.0955 wt. %, from 0.0005 wt. % to 0.1005 wt. %, from 0.0005 wt. % to 0.1055 wt. %, from 0.0005 wt. % to 0.1105 wt. %, from 0.0005 wt. % to 0.1155 wt. %, from 0.0005 wt. % to 0.1205 wt. %, from 0.0005 wt. % to 0.1255 wt. %, from 0.0005 wt. % to 0.1305 wt. %, from 0.0005 wt. % to 0.1355 wt. %, from 0.0005 wt. % to 0.1405 wt. %, from 0.0005 wt. % to 0.1455 wt. %, from 0.0005 wt. % to 0.1505 wt. %, from 0.0005 wt. % to 0.1555 wt. %, from 0.0005 wt. % to 0.1605 wt. %, from 0.0005 wt. % to 0.1655 wt. %, from 0.0005 wt. % to 0.1705 wt. %, from 0.0005 wt. % to 0.1755 wt. %, from 0.0005 wt. % to 0.1805 wt. %, from 0.0005 wt. % to 0.1855 wt. %, from 0.0005 wt. % to 0.1905 wt. %, from 0.0005 wt. % to 0.1955 wt. %, from 0.0005 wt. % to 0.2005 wt. %, from 0.0005 wt. % to 0.2055 wt. %, from 0.0005 wt. % to 0.2105 wt. %, from 0.0005 wt. % to 0.2155 wt. %, from 0.0005 wt. % to 0.2205 wt. %, from 0.0005 wt. % to 0.2255 wt. %, from 0.0005 wt. % to 0.2305 wt. %, from 0.0005 wt. % to 0.2355 wt. %, from 0.0005 wt. % to 0.2405 wt. %, from 0.0005 wt. % to 0.2455 wt. %, from 0.0005 wt. % to 0.2505 wt. %, from 0.0005 wt. % to 0.2555 wt. %, from 0.0005 wt. % to 0.2605 wt. %, from 0.0005 wt. % to 0.2655 wt. %, from 0.0005 wt. % to 0.2705 wt. %, from 0.0005 wt. % to 0.2755 wt. %, from 0.0005 wt. % to 0.2805 wt. %, from 0.0005 wt. % to 0.2855 wt. %, from 0.0005 wt. % to 0.2905 wt. %, from 0.0005 wt. % to 0.2955 wt. %, from 0.0005 wt % to 0.3005 wt. %, from 0.0005 wt. % to 0.3055 wt. %, from 0.0005 wt. % to 0.3105 wt. %, from 0.0005 wt. % to 0.3155 wt. %, from 0.0005 wt. % to 0.3205 wt. %, from 0.0005 wt. % to 0.3255 wt. %, from 0.0005 wt. % to 0.3305 wt. %, from 0.0005 wt. % to 0.3355 wt. %, from 0.0005 wt. % to 0.3405 wt. %, from 0.0005 wt. % to 0.3455 wt. %, from 0.0005 wt. % to 0.3505 wt. %, from 0.0005 wt. % to 0.3555 wt. %, from 0.0005 wt. % to 0.3605 wt. %, from 0.0005 wt. % to 0.3655 wt. %, from 0.0005 wt. % to 0.3705 wt. %, from 0.0005 wt. % to 0.3755 wt. %, from 0.0005 wt. % to 0.3805 wt. %, from 0.0005 wt. % to 0.3855 wt. %, from 0.0005 wt. % to 0.3905 wt. %, from 0.0005 wt. % to 0.3955 wt. %, from 0.0005 wt. % to 0.4005 wt. %, from 0.0005 wt. % to 0.4055 wt. %, from 0.0005 wt. % to 0.4105 wt. %, from 0.0005 wt. % to 0.4155 wt. %, from 0.0005 wt. % to 0.4205 wt. %, from 0.0005 wt. % to 0.4255 wt. %, from 0.0005 wt. % to 0.4305 wt. %, from 0.0005 wt. % to 0.4355 wt. %, from 0.0005 wt. % to 0.4405 wt. %, from 0.0005 wt. % to 0.4455 wt. %, from 0.0005 wt. % to 0.4505 wt. %, from 0.0005 wt. % to 0.4555 wt. %, from 0.0005 wt. % to 0.4605 wt. %, from 0.0005 wt. % to 0.4655 wt. %, from 0.0005 wt. % to 0.4705 wt. %, from 0.0005 wt. % to 0.4755 wt. %, from 0.0005 wt. % to 0.4805 wt. %, from 0.0005 wt. % to 0.4855 wt. %, from 0.0005 wt. % to 0.4905 wt. %, from 0.0005 wt. % to 0.4955 wt. %, from 0.0005 wt. % to 0.5005 wt. %, from 0.0005 wt. % to 0.5055 wt. %, from 0.0005 wt. % to 0.5105 wt. %, from 0.0005 wt. % to 0.5155 wt. %, from 0.0005 wt. % to 0.5205 wt. %, from 0.0005 wt. % to 0.5255 wt. %, from 0.0005 wt. % to 0.5305 wt. %, from 0.0005 wt. % to 0.5355 wt. %, from 0.0005 wt. % to 0.5405 wt. %, from 0.0005 wt. % to 0.5455 wt. %, from 0.0005 wt. % to 0.5505 wt. %, from 0.0005 wt. % to 0.5555 wt. %, from 0.0005 wt. % to 0.5605 wt. %, from 0.0005 wt. % to 0.5655 wt. %, from 0.0005 wt. % to 0.5705 wt. %, from 0.0005 wt. % to 0.5755 wt. %, from 0.0005 wt. % to 0.5805 wt. %, from 0.0005 wt. % to 0.5855 wt. %, from 0.0005 wt. % to 0.5905 wt. %, from 0.0005 wt. % to 0.5955 wt. %, from 0.0005 wt. % to 0.6005 wt. %, from 0.0005 wt. % to 0.6055 wt. %, from 0.0005 wt. % to 0.6105 wt. %, from 0.0005 wt. % to 0.6155 wt. %, from 0.0005 wt. % to 0.6205 wt. %, from 0.0005 wt. % to 0.6255 wt. %, from 0.0005 wt. % to 0.6305 wt. %, from 0.0005 wt. % to 0.6355 wt. %, from 0.0005 wt. % to 0.6405 wt. %, from 0.0005 wt. % to 0.6455 wt. %, from 0.0005 wt. % to 0.6505 wt. %, from 0.0005 wt. % to 0.6555 wt. %, from 0.0005 wt. % to 0.6605 wt. %, from 0.0005 wt. % to 0.6655 wt %, from 0.0005 wt. % to 0.6705 wt. %, from 0.0005 wt. % to 0.6755 wt. %, from 0.0005 wt. % to 0.6805 wt. %, from 0.0005 wt. % to 0.6855 wt. %, from 0.0005 wt. % to 0.6905 wt. %, from 0.0005 wt. % to 0.6955 wt. %, from 0.0005 wt. % to 0.7005 wt. %, from 0.0005 wt. % to 0.7055 wt. %, from 0.0005 wt. % to 0.7105 wt. %, from 0.0005 wt. % to 0.7155 wt. %, from 0.0005 wt. % to 0.7205 wt. %, from 0.0005 wt. % to 0.7255 wt. %, from 0.0005 wt. % to 0.7305 wt. %, from 0.0005 wt. % to 0.7355 wt. %, from 0.0005 wt. % to 0.7405 wt. %, from 0.0005 wt. % to 0.7455 wt %, from 0.0005 wt. % to 0.7505 wt. %, from 0.0005 wt. % to 0.7555 wt. %, from 0.0005 wt. % to 0.7605 wt,%, from 0.0005 wt. % to 0.7655 wt. %, from 0.0005 wt. % to 0.7705 wt. %, from 0.0005 wt. % to 0.7755 wt. %, from 0.0005 wt. % to 0.7805 wt. %, from 0.0005 wt. % to 0.7855 wt. %, from 0.0005 wt. % to 0.7905 wt. %, from 0.0005 wt. % to 0.7955 wt. %, from 0.0005 wt. % to 0.8005 wt. %, from 0.0005 wt. % to 0.8055 wt. %, from 0.0005 wt. % to 0.8105 wt. %, from 0.0005 wt. % to 0.8155 wt. %, from 0.0005 wt. % to 0.8205 wt. %, from 0.0005 wt. % to 0.8255 wt. %, from 0.0005 wt. % to 0.8305 wt. %, from 0.0005 wt. % to 0.8355 wt. %, from 0.0005 wt. % to 0.8405 wt. %, from 0.0005 wt. % to 0.8455 wt. %, from 0.0005 wt. % to 0.8505 wt. %, from 0.0005 wt. % to 0.8555 wt. %, from 0.0005 wt. % to 0.8605 wt. %, from 0.0005 wt. % to 0.8655 wt. %, from 0.0005 wt. % to 0.8705 wt. %, from 0.0005 wt. % to 0.8755 wt. %, from 0.0005 wt. % to 0.8805 wt. %, from 0.0005 wt. % to 0.8855 wt. %, from 0.0005 wt. % to 0.8905 wt. %, from 0.0005 wt. % to 0.8955 wt. %, from 0.0005 wt. % to 0.9005 wt. %, from 0.0005 wt. % to 0.9055 wt %, from 0.0005 wt. % to 0.9105 wt. %, from 0.0005 wt. % to 0.9155 wt. %, from 0.0005 wt. % to 0.9205 wt. %, from 0.0005 wt. % to 0.9255 wt. %, from 0.0005 wt. % to 0.9305 wt. %, from 0.0005 wt. % to 0.9355 wt. %, from 0.0005 wt. % to 0.9405 wt. %, from 0.0005 wt % to 0.9455 wt. %, from 0.0005 wt. % to 0.9505 wt. %, from 0.0005 wt. % to 0.9555 wt. %, from 0.0005 wt. % to 0.9605 wt. %, from 0.0005 wt. % to 0.9655 wt. %, from 0.0005 wt. % to 0.9705 wt. %, from 0.0005 wt. % to 0.9755 wt. %, from 0.0005 wt. % to 0.9805 wt. %, from 0.0005 wt. % to 0.9855 wt. %, from 0.0005 wt. % to 0.9905 wt. %, from 0.0005 wt. % to 0.9955 wt. %, and from 0.0005 wt. % to 1 wt. %.

Generally, with the alloy compositions of the present invention are based on a monophasic material free of secondary phases which otherwise act as cathodic microgalvanic cells. To achieve the necessary purity level of the MgZn, MgZnCa alloy embodiments described herein, the acceptable amount of other elements within the alloy is limited.

In one embodiment, the MgZn alloy contains less than 5 ppm of total other elements. In another embodiment, the MgZn alloy contains less than 2 ppm of total other elements. In yet another embodiment, the MgZn alloy contains less than 1 ppm of total other elements. In still yet another embodiment, the MgZn alloy contains less than 0.5 ppm of total other elements.

In one embodiment, the MgZnCa alloy, having a plurality of nanosized precipitates being less noble than a MgZn alloy, contains less than 5 ppm of total other elements. In another embodiment, the MgZnCa alloy, having a plurality of nanosized precipitates being less noble than a MgZn alloy, contains less than 2 ppm of total other elements. In yet another embodiment, the MgZnCa alloy, having a plurality of nanosized precipitates being less noble than a MgZn alloy, contains less than 1 ppm of total other elements. In still yet another embodiment, the MgZnCa alloy, having a plurality of nanosized precipitates being less noble than a MgZn alloy, contains less than 0.5 ppm of total other elements.

In one embodiment, the MgZnCa alloy, having a plurality of nanosized precipitates being less noble than a MgZn alloy and a plurality of nanosized precipitates being more noble than a MgZn alloy, contains less than 5 ppm of total other elements. In another embodiment, the MgZnCa alloy, having a plurality of nanosized precipitates being less noble than a MgZn alloy and a plurality of nanosized precipitates being more noble than a MgZn alloy, contains less than 2 ppm of total other elements. In yet another embodiment, the MgZnCa alloy, having a plurality of nanosized precipitates being less noble than a MgZn alloy and a plurality of nanosized precipitates being more noble than a MgZn alloy, contains less than 1 ppm of total other elements. In still yet another embodiment, the MgZnCa alloy, having a plurality of nanosized precipitates being less noble than a MgZn alloy and a plurality of nanosized precipitates being more noble than a MgZn alloy, contains less than 0.5 ppm of total other elements.

In such embodiments, the other elements include one or more of Fe, Cu, Ni, Co, Si, Mn, Al, Zr and P.

In another embodiment, the MgZn alloy contains less than 5 ppm Fe content. In another embodiment, the MgZn alloy contains less than 5 ppm Si content. In another embodiment, the MgZn alloy contains less 5 ppm Mn content. In yet another embodiment, the MgZn alloy contains less than 2 ppm Co content. In another embodiment, the MgZn alloy contains less than 2 ppm Ni. In another embodiment, the MgZn alloy contains less than 0.1 ppm Ni. In another embodiment, the MgZn alloy contains less 2 ppm Cu content. In yet another embodiment, the MgZn alloy contains less 10 ppm Al content.

In another embodiment, the MgZnCa alloy, having a plurality of nanosized precipitates being less noble than a MgZn alloy, contains less than 5 ppm Fe content. In another embodiment, the MgZn alloy contains less than 5 ppm Si content. In another embodiment, the MgZnCa alloy, having a plurality of nanosized precipitates being less noble than a MgZn alloy, contains less 5 ppm Mn content. In yet another embodiment, the MgZnCa alloy, having a plurality of nanosized precipitates being less noble than a MgZn alloy, contains less than 2 ppm Co content. In another embodiment, the MgZnCa alloy, having a plurality of nanosized precipitates being less noble than a MgZn alloy, contains less than 2 ppm Ni. In another embodiment, the MgZnCa alloy, having a plurality of nanosized precipitates being less noble than a MgZn alloy, contains less than 0.1 ppm Ni. In another embodiment, the MgZnCa alloy, having a plurality of nanosized precipitates being less noble than a MgZn alloy, contains less 2 ppm Cu content. In yet another embodiment, the MgZnCa alloy, having a plurality of nanosized precipitates being less noble than a MgZn alloy, contains less 10 ppm Al content.

In another embodiment, the MgZnCa alloy, having a plurality of nanosized precipitates being less noble than a MgZn alloy and a plurality of nanosized precipitates being more noble than a MgZn alloy, contains less than 5 ppm Fe content. In another embodiment, the MgZn alloy contains less than 5 ppm Si content. In another embodiment, the MgZnCa alloy, having a plurality of nanosized precipitates being less noble than a MgZn alloy and a plurality of nanosized precipitates being more noble than a MgZn alloy, contains less 5 ppm Mn content. In yet another embodiment, the MgZnCa alloy, having a plurality of nanosized precipitates being less noble than a MgZn alloy and a plurality of nanosized precipitates being more noble than a MgZn alloy, contains less than 2 ppm Co content. In another embodiment, the MgZnCa alloy, having a plurality of nanosized precipitates being less noble than a MgZn alloy and a plurality of nanosized precipitates being more noble than a MgZn alloy, contains less than 2 ppm Ni. In another embodiment, the MgZnCa alloy, having a plurality of nanosized precipitates being less noble than a MgZn alloy and a plurality of nanosized precipitates being more noble than a MgZn alloy, contains less than 0.1 ppm Ni. In another embodiment, the MgZnCa alloy, having a plurality of nanosized precipitates being less noble than a MgZn alloy and a plurality of nanosized precipitates being more noble than a MgZn alloy, contains less 2 ppm Cu content. In yet another embodiment, the MgZnCa alloy, having a plurality of nanosized precipitates being less noble than a MgZn alloy and a plurality of nanosized precipitates being more noble than a MgZn alloy, contains less 10 ppm Al content.

The impurity level is maintained at such levels to control the corrosion rate once an implant, based on such alloys, is place in the body. It is necessary to control the corrosion rate so that the implant possesses sufficient strength over a period of time to allow healing and so not to interfere with the healing process. Although the degradation by-products from the magnesium alloys of the present invention are non-toxic, as the metal corrodes the pH near the implant increases to a basic pH. Likewise, hydrogen gas produced during the corrosion process must be eliminated. In the case endovascular implants, these concerns are insignificant as the constant blood flow over the implant removes the hydrogen gas and other degradation by-products.

Generally, the rare earth content in the various embodiments of the MgZn alloy, the MgZnCa alloys and the MgZn alloy, the MgZnCa alloys compositions used in an implant, according to the present invention is limited. In such embodiments, the rare earth elements include Sc, Y, the Lanthanide elements, atomic numbers ranging from 57-71 and the Actinide elements, atomic numbers ranging from 89-103. In one embodiment, the rare earth content is less than 10 ppm. In another embodiment, the rare earth content is less than 5 ppm. In some embodiments, the rare earth content is less than 1 ppm, less than 0.5 ppm, less than 0.1 ppm, or less than 0.05 ppm.

The mechanical properties of the ultrapure magnesium are improved by solid solution hardening with high purity zinc without affecting the monophasic nature of the alloy. A fine grained microstructure can be achieved by severe plastic deformation and stabilized with secondary phases which are less noble than the magnesium matrix. For example, the less noble $Mg_6Zn_3Ca_2$ phase can be obtained by small additions of high purity calcium and adequate heat treatment. If needed, the degradation rate can be accelerated, while maintaining a uniform corrosion profile, by an aging heat treatment below 250° C., which forms fine metastable MgZn precipitates.

Implants made from the compositions described herein have advantageous physical properties, including high yield strength, high ultimate tensile strength, and elongation at break. In some embodiments, each alloy has the yield strength of at least 200 MPa. In other embodiments, each alloy has a yield strength of at least at least 220 MPa, at least 240 MPa, at least 250 MPa, at least 260 MPa, at least 280 MPa, at least 300 MPa, at least 320 MPa, at least 340 MPa, at least 360 MPa, or at least 380 MPa. In some embodiments, each alloy has an ultimate tensile strength of at least 250 MPa. In other embodiments, each alloy has an ultimate tensile strength of at least 260 MPa, at least 280 MPa, at least 300 MPa, at least 320 MPa, at least 340 MPa, at least 360 MPa, or at least 380 MPa. In some embodiments, each alloy has at least 15% elongation at break. In other embodiments, each alloy has at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% elongation at break.

Implants according exemplary embodiments of the present invention also have advantageous chemical properties in vitro and in vivo. In some embodiments, each alloy has an in vitro degradation rate of less than 0.5 mg/cm$^2$ day as measured in a simulated body fluid. In other embodiments, each alloy has an in vitro degradation rate of less than 0.05 mg/cm$^2$ day, less than 0.1 mg/cm$^2$ day, less than 0.15 mg/cm$^2$ day, less than 0.2 mg/cm$^2$ day, less than 0.25 mg/cm$^2$ day, less than 0.3 mg/cm$^2$ day, less than 0.35 mg/cm$^2$ day, less than 0.4 mg/cm$^2$ day, or less than 0.45 mg/cm$^2$ day, as measured in a simulated body fluid.

Implantable medical devices based on the compositions described herein can be manufactured for a variety of medical/clinical applications, including replacing a missing biological structure, to support a damaged biological structure, or to enhance an existing biological structure. The composition of the implants and/or the surfaces of the implants that contact the body/body tissues can be varied depending on the particular application under consideration. Surgical implants can be manufactured for medical/clinical applications in the area of orthopedics, neurosurgery, among others. Non-limiting examples of surgical implants include: neurosurgical implants, e.g. hydrocephalus shunts and components; intracranial aneurysm clips; bone and joint replacements, e.g., partial and total hip joint prostheses and total knee-joint prostheses; osteosynthesis and spinal devices, e.g., metal bone screws, metal bone plates, medullary pins, metallic skeletal pins and wires, and total intervertebral spinal disc prostheses; oral and maxillo facial surgery implants; and spinal and pelvic systems such as Universal Spine System, Harrington System, and conventional systems. Accordingly, surgical implants that can be manufactured based on the compositions described herein can include a wide range of products varying in composition as described herein, structural complexity and medical/clinical applications. As such, implants for use in accordance with exemplary embodiments of the present invention can vary in size, shape, and other physical and chemical characteristics depending upon the context of use.

In some embodiments, the implant is an orthopedic implant. In such embodiments, the orthopedic implant comprises one or more of the following: a nail, a screw, a staple, a plate, a rod, a tack, a bolt, a bolt to lock and IM nail, an anchor, a dowel, a plug, a peg, a sleeve, a mesh, a transconnector, a nut, a shaped body, spinal cage, a wire, a K-wire, a woven structure, clamp, splint, scaffold, foam and honeycomb structure. In some other embodiments, the implant has a lower degradation rate compared to magnesium alloy implants containing microgalvanic impurities.

In other embodiments, the implant is a non-orthopedic implant. In such embodiments, the non-orthopedic includes a cardiovascular stent, a neuro stent and a vertebroplasty stent.

Corrosion rate of magnesium strongly depends on its purity. In a 4% water solution of sodium chloride, a corrosion rate of magnesium of purity of 99.9% is reportedly hundreds of times higher than for magnesium with purity of 99.99%.

In vitro degradation tests in simulated body fluid (SBF) show that a uniform degradation with extremely low degradation rate can be achieved when using such ultrapure magnesium. However, ultrapure magnesium has poor mechanical properties in comparison to alloys like WE43. This limitation, it has been discover, can be overcome this limitation, through hardening of the alloy. The hardening of the alloy can be achieved by refining the grain microstructure using severe plastic deformation (ECAP, extrusion, etc.). In addition to achieving a better strength level, the fine grained microstructure was also found to avoid mechanical anisotropy (strength difference between tension and compression).

It was also found that hardening of the magnesium matrix could be achieved by way of a solid solution with a highly pure alloying element such as zinc. The phase diagram for Mg—Zn shows a maximum solubility of 6.2 wt % Zn at the eutectic temperature. After alloying magnesium with for example 5 wt. % Zn, the material could be homogenized by a two step solution heat treatment, with a first temperature below and a second temperature above the eutectic temperature. The resulting monophasic alloy was found to exhibit very uniform and slow degradation.

In an aspect, the present invention provides a method of producing an alloy according to the embodiments described herein. In one embodiment, the method comprises: (a) casting a alloy containing (i) ultrapure magnesium having a purity of at least 99.997 wt. % and having less than 0.001 wt. % of one or more other elements; and (ii) from 2.0 to 6 wt. % zinc having a purity of at least 99.999 wt. %, said casting being performed in an inert atmosphere and an inert reaction vessel; (b) heating the cast alloy at two different temperatures wherein a first temperature is below an eutectic temperature of Mg—Zn and a second temperature is above the eutectic temperature of the ternary Mg—Zn—Ca system to thereby form a monophasic MgZn alloy containing from 2.0 wt. % Zn to 6 wt. % Zn, having less than 0.001 wt. % of one or more other elements with the remainder being Mg; and (c) extruding the alloy into a desired shape.

In some embodiments, the method of producing an alloy according the present invention comprises: (a) casting a alloy containing (i) ultrapure magnesium having a purity of at least 99.997 wt. % and having less than 0.001 wt. % of one or more other elements; (ii) from 3.0 wt. zinc to 6 wt. % zinc having a purity of at least 99.999 wt. %; and (iii) from 0.02 wt. % to 1.0 wt. % calcium metal having a purity of at least 99.9 wt. %, said casting being performed in an inert atmosphere and an inert reaction vessel; (b) heating the cast alloy at two different temperatures wherein a first temperature is below an eutectic temperature of Mg—Zn and a second temperature is above the eutectic temperature of the ternary Mg—Zn—Ca system to thereby form a MgZnCa alloy containing from 3.0 wt. % Zn to 6 wt. % Zn; a calcium content ranging from 0.0005 wt. % to 1.0 wt. %, having less than 0.001 wt. % of one or more other elements with the remainder being Mg, (c) extruding the alloy into a desired shape; and (d) heating the shaped alloy to at least 140° C. to form more noble nanosized precipitates dispersed throughout a MgZnCa alloy. In a further embodiment, the method comprises heating to at least 230° C. to form more noble precipitates dispersed throughout a MgZn alloy.

Not wishing to be bound by theory, it believed it might advantageous for stable fine grained microstructure of the alloy if the grain boundaries are be pinned. The pinning could be achieved by fine precipitates which are less noble than the magnesium matrix and, as a consequence, do not deteriorate the degradation performance of the material. $Mg_6Zn_3Ca_2$ is one of the few phases which are electrochemically less noble than pure magnesium. With the addition of 0.25 wt % Ca, such finely dispersed precipitates can be created by an aging heat treatment (following the initial solution heat treatment). If the degradation rate of the alloy is too slow and needs to be accelerated, very fine metastable MgZn precipitates can be formed by applying an aging heat treatment at temperatures below 250° C. With increasing size, these precipitates start to act as cathodic microgalvanic elements and accelerate the corrosion in a controllable manner.

The magnesium alloys in the exemplary embodiments described above have especially favorable properties for processing and for their later intended purpose in comparison with traditional magnesium alloys: the ductility of the magnesium alloys is greatly elevated. For purposes of the present disclosure, the term "ductility" (or toughness, deformation capacity) refers to the ability of a metallic material to undergo permanent deformation under sufficiently high mechanical loads before cracking occurs. This ability is of great importance for many construction parts because only a ductile material is capable of dissipating local mechanical stress peaks by undergoing permanent deformation without cracking and with simultaneous cold solidification. This aspect, in particular, makes it especially advantageous to use the inventive magnesium alloys as a material, for example, for biodegradable implants, in particular, biodegradable bone fixation implants. With a given material, the ductility depends on the temperature, the stress rate, the multi-axle character of the acting mechanical stress state and the environment. Characteristic values of ductility include, e.g., the elongation at break and necking, the notched impact strength and the fracture toughness as described elsewhere herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A medical implant comprising:
a MgZnCa alloy containing nanosized precipitates, wherein the nanosized precipitates are less noble than a MgZn alloy, and wherein the MgZnCa alloy has a Zn content ranging from 3.0 wt. % Zn to 6 wt. % Zn and a calcium content ranging from 0.0005 wt. % Ca to 1.0 wt. % Ca, less than 0.001 wt. % of one or more other elements and with the remainder of the alloy being Mg, wherein the Mg has a purity of at least 99.997 wt. %, the Zn has a purity of at least 99.999 wt. %, and the Ca has a purity of at least 99.9 wt. %.

2. The implant according to claim 1, wherein the MgZnCa alloy contains less than 5 ppm of total other elements.

3. The implant according to claim 1, wherein the MgZnCa alloy contains less than 2 ppm of total other elements.

4. The implant according to claim 1, wherein the MgZnCa alloy contains less than 1 ppm of total other elements.

5. The implant according to claim 1, wherein the MgZnCa alloy contains less than 0.5 ppm of total other elements.

6. The implant according to claim 1, wherein the other elements comprise one or more of Fe, Cu, Ni, Co, Si, Mn, Al, Zr, and P.

7. The implant according to claim 1, wherein the MgZnCa alloy contains less than 0.1 ppm Ni.

8. The implant according to claim 1, wherein the MgZnCa alloy contains less than 0.001 wt. % of rare earth elements.

9. The implant according to claim 8, wherein the rare earth elements comprise one or more of Sc, Y, the Lanthanide elements having atomic numbers ranging from 57-71, and the Actinide elements having atomic numbers ranging from 89-103.

10. The implant according to claim 1, further comprising a plurality of nanosized precipitates being more noble than the MgZn alloy, wherein the nanosized precipitates comprise Mn—Zn.

11. The implant according to claim 1, wherein the MgZnCa alloy has a grain size of less than 10 μm.

12. The implant according to claim 1, wherein the MgZnCa alloy has a yield strength of at least 200 MPa.

13. The implant according to claim 1, wherein the MgZnCa alloy has an ultimate tensile strength of at least 250 MPa.

14. The implant according to claim 1, wherein the MgZnCa alloy has at least 15% elongation at break.

15. A medical implant comprising: a MgZnCa alloy, having a Zn content ranging from 3.0 wt. % Zn to 6 wt. % Zn, the Zn having a purity of at least 99.999 wt. %, a calcium content ranging from 0.0005 wt. % Ca to 1.0 wt. % Ca, the Ca having a purity of at least 99.9 wt. %, less than 0.001 wt. % of one or more other elements located in a secondary phase and with the remainder of the alloy being Mg having a purity of at least 99.997 wt. %, wherein the MgZnCa alloy contains nanosized precipitates being less noble than the Mg remainder.

* * * * *